(12) United States Patent
Lee et al.

(10) Patent No.: US 9,823,206 B2
(45) Date of Patent: Nov. 21, 2017

(54) APPARATUS AND METHOD FOR MEASURING OVERALL HEAT TRANSFER COEFFICIENT

(71) Applicant: Kyungpook National University Industry-Academic Cooperation Foundation, Daegu (KR)

(72) Inventors: Hyun Woo Lee, Daegu (KR); Jong Won Lee, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 637 days.

(21) Appl. No.: 14/331,111

(22) Filed: Jul. 14, 2014

(65) Prior Publication Data
US 2016/0011130 A1 Jan. 14, 2016

(51) Int. Cl.
*G01N 25/18* (2006.01)
*G01K 17/02* (2006.01)
*G01K 17/06* (2006.01)
*G01K 17/20* (2006.01)

(52) U.S. Cl.
CPC .............. *G01N 25/18* (2013.01); *G01K 17/20* (2013.01)

(58) Field of Classification Search
CPC .............................. G01N 25/18; G01K 17/02
USPC .... 374/29, 30, 4, 5, 44, 137, 109, 121, 100, 374/1, 2, 208; 324/557
See application file for complete search history.

(56) References Cited

U.S. PATENT DOCUMENTS

| | | | | |
|---|---|---|---|---|
| 2,239,128 A | * | 4/1941 | Sykes | ...................... B65D 7/22 |
| | | | | 220/592.21 |
| 3,453,865 A | * | 7/1969 | Reiter | .................... G01N 25/72 |
| | | | | 374/29 |
| 4,323,620 A | * | 4/1982 | Iwabuchi | ................ B32B 15/14 |
| | | | | 220/62.15 |

(Continued)

FOREIGN PATENT DOCUMENTS

| | | |
|---|---|---|
| JP | 2004257898 A | 9/2004 |
| KR | 20050015813 A | 2/2005 |

OTHER PUBLICATIONS

Diop et al., "Over Heat Transfer Coefficient Measurement of Covering Materials with Thermal Screens for Greenhouse using the Hot Box Method", Journal of the Korean Society of Agricultural Engineers, vol. 54, No. 5, Sep. 2012, 7 pages.

*Primary Examiner* — Gail Kaplan Verbitsky
(74) *Attorney, Agent, or Firm* — McCoy Russell LLP

(57) ABSTRACT

An apparatus for measuring an overall heat transfer coefficient may include an external chamber provided using a heat insulation material and including an internal space, an internal chamber disposed in the external chamber and having an opening upper portion, a heat source supply to supply heat to an internal portion of the internal chamber, a cutoff portion disposed in the upper portion of the internal chamber to seal the internal chamber and prevent an outflow of heat emitted from the heat source supply, and a temperature measurement portion disposed in an internal portion and an external portion of the internal chamber to measure an internal temperature and an external temperature of the internal chamber, in which the cutoff portion may realize covering conditions indoors through a combination of a covering material and a thermal screen, and adjust the external temperature of the internal chamber.

7 Claims, 8 Drawing Sheets

(56) References Cited

U.S. PATENT DOCUMENTS

| | | | | |
|---|---|---|---|---|
| 4,647,221 A | * | 3/1987 | Szabo | G01N 25/18 |
| | | | | 374/30 |
| 4,670,404 A | * | 6/1987 | Swift | B01J 3/002 |
| | | | | 374/33 |
| 6,585,408 B2 | * | 7/2003 | El-Gabry | G01N 25/18 |
| | | | | 374/162 |
| 6,977,469 B2 | * | 12/2005 | Seinen | H01J 61/04 |
| | | | | 313/492 |
| 8,215,835 B2 | * | 7/2012 | Hyde | A61B 19/026 |
| | | | | 220/592.2 |
| 2003/0072349 A1 | * | 4/2003 | Osone | G01N 25/18 |
| | | | | 374/43 |
| 2009/0154520 A1 | * | 6/2009 | Richner | G01N 25/005 |
| | | | | 374/29 |
| 2016/0327439 A1 | * | 11/2016 | Pandraud | G01K 17/20 |
| 2017/0191765 A1 | * | 7/2017 | Lee | F28F 13/02 |

* cited by examiner

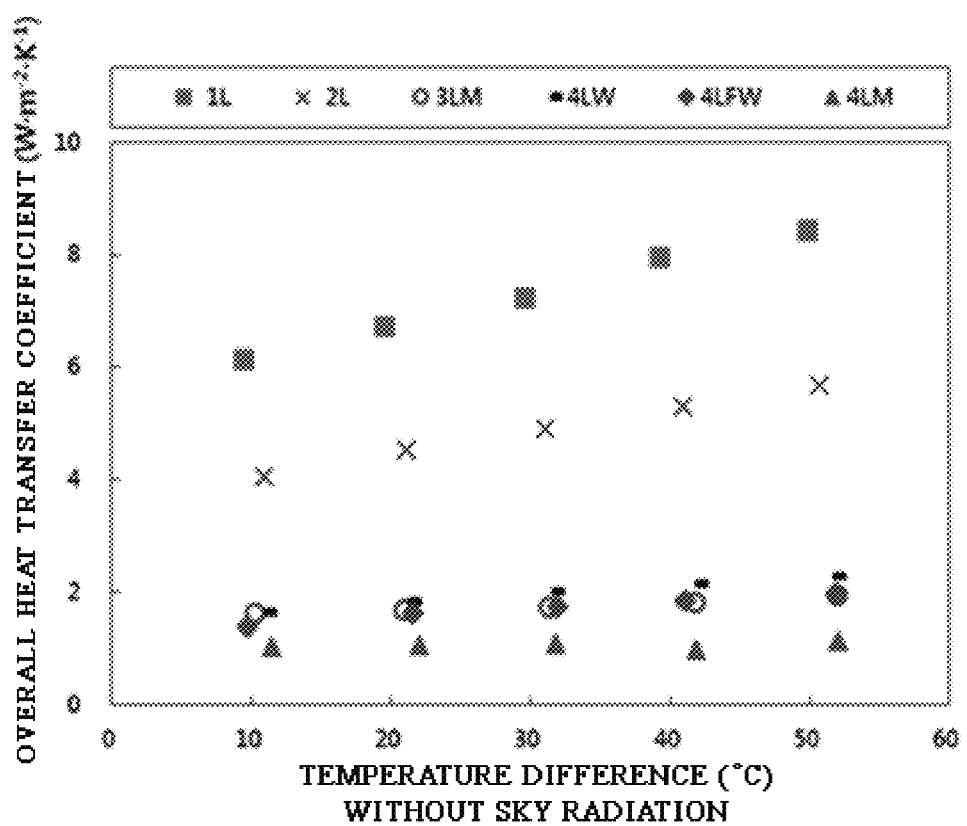

APPARATUS AND METHOD FOR MEASURING OVERALL HEAT TRANSFER COEFFICIENT

BACKGROUND

1. Field of the Invention

Embodiments of the present invention relate to an apparatus and method for measuring an overall heat transfer coefficient, and more particularly, to an apparatus and method for measuring an overall heat transfer coefficient that may measure a heat transfer characteristic of a covering material and a thermal screen indoors by realizing various covering conditions using a combination of the covering material and the thermal screen.

2. Description of the Related Art

A greenhouse refers to a facility in which a cultivation space isolated from outside weather is created by covering an area with glass or a plastic film. In the greenhouse, crops are produced by artificially adjusting environments, for example, micrometeorological conditions or internal medium conditions, using a variety of supplementary equipment.

In general, an actual greenhouse may be covered with an external covering material and an internal thermal screen to minimize an external loss of heat from the greenhouse and maintain growing environment conditions, for example, a desired temperature and humidity level of the greenhouse, to be suitable for growing crops.

Heat externally lost from such a greenhouse includes convective heat, radiant heat, and conductive heat.

The convective heat refers to a transfer of heat by a temperature difference between a solid surface and a fluid. The radiant heat refers to heat produced when heat emitted from a heat source of a relatively high-temperature object passes through a space and is absorbed into a relatively low-temperature object. The conductive heat refers to a transfer of thermal energy in a solid from relatively high temperature to relatively low temperature.

However, in practice, a loss of heat by a sky radiation is relatively significant in a case of a greenhouse used for agriculture.

Thus, a covering material or a thermal screen suitable for a greenhouse is to be selected in view of effects of such a sky radiation.

As an example, Japanese Patent Application No. JP2004-257898, filed on Sep. 6, 2014, discloses "Method and apparatus for testing heat insulation performance of heat insulation material".

SUMMARY

An aspect of the present invention provides an apparatus and method for measuring an overall heat transfer coefficient that may suggest a quantitative heat insulation performance of a covering material or a thermal screen by measuring an overall heat transfer coefficient of the covering material or the thermal screen.

Another aspect of the present invention also provides an apparatus and method for measuring an overall heat transfer coefficient that may establish standards of a covering material or a thermal screen for a greenhouse.

Still another aspect of the present invention also provides an apparatus and method for measuring an overall heat transfer coefficient that may accurately calculate a heating load of an actual greenhouse.

Yet another aspect of the present invention also provides an apparatus and method for measuring an overall heat transfer coefficient that may simply realize various covering conditions of a greenhouse.

According to an aspect of the present invention, there is provided an apparatus for measuring an overall heat transfer coefficient, the apparatus including an external chamber provided using a heat insulation material and including an internal space, an internal chamber disposed in the external chamber and having an opening upper portion, a heat source supply to supply heat to an internal portion of the internal chamber, a cutoff portion disposed in the upper portion of the internal chamber to seal the internal chamber and prevent an outflow of heat emitted from the heat source supply, and a temperature measurement portion disposed in an internal portion and an external portion of the internal chamber to measure an internal temperature and an external temperature of the internal chamber. The cutoff portion may realize covering conditions indoors through a combination of a covering material and a thermal screen, and adjusts the external temperature of the internal chamber.

A sky radiation realization portion may be provided above the cutoff portion to realize a sky radiation, a pipe may be provided in the sky radiation realization portion to exchange heat, and a sky temperature may be realized through a working fluid circulating through the pipe.

The apparatus may further include a temperature adjustment portion disposed internally of the external chamber to adjust an internal temperature of the external chamber.

The covering material may include a polyethylene film, the thermal screen may include a multilayer thermal screen, white polyester, and white fabric polyester, and the sky radiation realization portion may be provided using stainless steel.

A plurality of spacers may be provided internally of the internal chamber to enable the covering material and the thermal screen to be detachably disposed and separated from each other in a vertical direction in the internal chamber.

The temperature measurement portion may include a plurality of sensors, and the plurality of sensors may be disposed internally and externally of side walls and a bottom surface of the internal chamber to determine the internal temperature of the internal chamber by calculating an average of values measured inside the internal chamber, and determine the external temperature of the internal chamber by calculating an average of values measured outside the internal chamber.

According to another aspect of the present invention, there is also provided a method of measuring an overall heat transfer coefficient, the method including providing an apparatus for measuring an overall heat transfer coefficient, the apparatus including an external chamber provided using a heat insulation material, and an internal chamber disposed in the external chamber, selecting a combination of a covering material and a thermal screen to be disposed in an upper portion of the internal chamber, supplying heat to an internal portion of the internal chamber, measuring an internal temperature and an external temperature of the internal chamber, and calculating the overall heat transfer coefficient based on the measured values.

The method may further include disposing a sky radiation realization portion above the covering material or the thermal screen to realize a sky temperature.

The calculating may include calculating the overall heat transfer coefficient by dividing a difference between a quantity of heat supplied to the internal chamber and a heat loss dissipated through the internal chamber by a difference between the internal temperature and the external temperature of the internal chamber and an area of the covering material or the thermal screen.

BRIEF DESCRIPTION OF THE DRAWINGS

FIGS. 4A and 4B illustrate changes in an overall heat transfer coefficient with respect to a difference between an internal temperature and an external temperature of an internal chamber of an apparatus for measuring an overall heat transfer coefficient according to an embodiment of the present invention;

DETAILED DESCRIPTION

Figure 1:
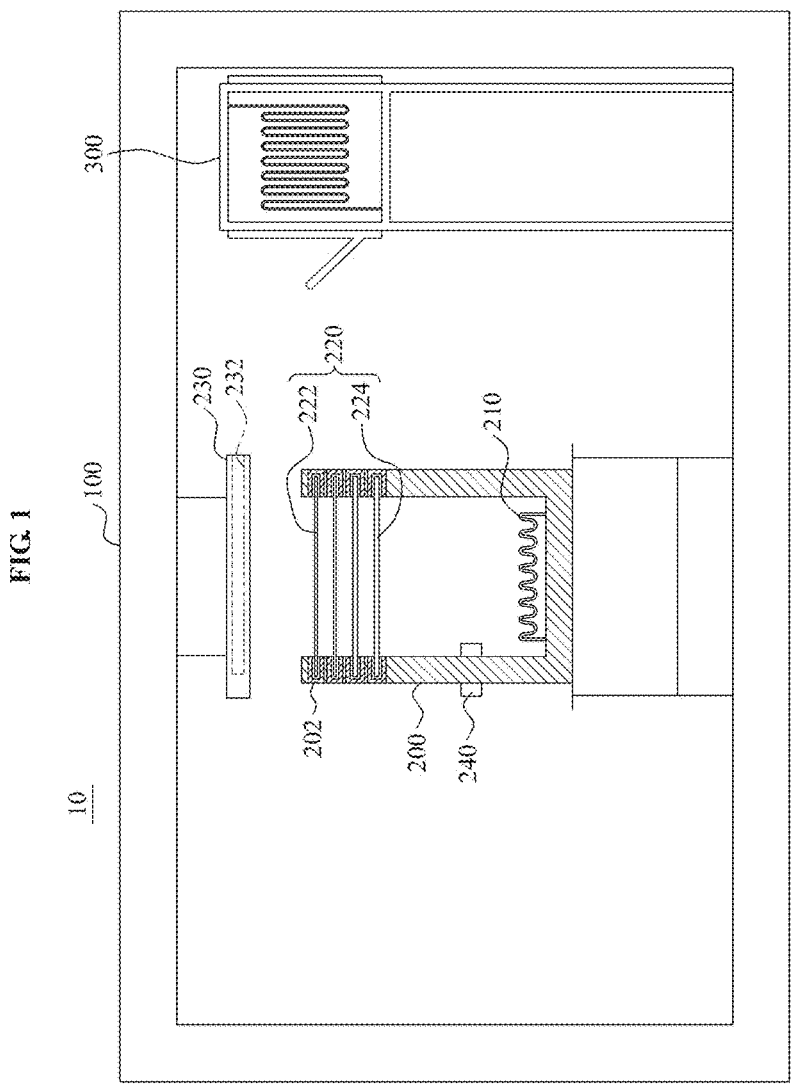
FIG. 1 is a diagram illustrating an apparatus for measuring an overall heat transfer coefficient according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a diagram illustrating an apparatus 10 for measuring an overall heat transfer coefficient according to an embodiment of the present invention.

Referring to FIG. 1, the apparatus 10 for measuring an overall heat transfer coefficient, hereinafter simply referred to as the apparatus 10, may include an external chamber 100, an internal chamber 200, and a temperature adjustment portion 300.

The external chamber 100 may be provided using a heat insulation material.

The external chamber 100 may be provided in a form of a box including four side walls, a bottom surface, and a top surface, and manufactured using polystyrene foam.

The external chamber 100 may include an internal space, and other constituent elements may be disposed in the external chamber 100.

To this end, an aperture (not shown) may be formed for an access to an internal portion of the external chamber 100. The other constituent elements may be moved inside the external chamber 100 through the aperture.

An airtight door may be provided on the aperture to cut off a heat exchange between the internal portion and an external portion of the external chamber 100.

The internal chamber 200 may be disposed in the external chamber 100.

The internal chamber 200 may correspond to a hot box partially manufactured and designed based on the American Society for Testing and Materials (ASTM) standards.

The internal chamber 200 may be provided in a form of a box including a bottom surface and four side walls, and having an opening upper portion. The internal chamber 200 may be provided using a heat insulation material including urethane.

A spacer 202 may be provided on a side wall of the internal chamber 200.

The spacer 202 refers to a liner having gaps into which constituent elements assembled alongside one another are to be inserted to maintain a uniform distance between the constituent elements. The spacer 202 may be provided to enable constituent elements of a cutoff portion 220 to be disposed to be separated from each other in a vertical direction.

A plurality of spacers 202 may be provided to be disposed at identical heights on both side walls that face each other. To dispose the cutoff portion 220 in opening spaces of the spacer 202, the spacer 202 may be disposed so that the opening spaces of the spacer 202 provided on both side walls may face each other.

The cutoff portion 220 may include a covering material 222 or a thermal screen 224. By the spacer 202, the covering material 222 and the thermal screen 224 may be provided in the internal chamber 20 to be equally separated from each other in a vertical direction. Since the covering material 222 or the thermal screen 224 may be detachable from the spacer 202, various combinations of the covering material 222 and the thermal screen 224 may be realized based on test conditions.

A heat source supply 210, the cutoff portion 220, a sky radiation realization portion 230, and a temperature measurement portion 240 may be provided in the internal chamber 200.

The heat source supply 210 may be disposed in the internal chamber 200, for example, on the bottom surface of the internal chamber 200.

The heat source supply 210 may include a heating coil that emits heat using electricity supplied by a power supply (not shown).

By applying heat to an internal portion of the internal chamber 200, the heat source supply 210 may increase an internal temperature of the internal chamber 200. In this example, power may be adjusted within a range between 0 to 500 watts (W) by a voltage adjuster (not shown) connected to the power supply, and the internal temperature of the internal chamber 200 may be predetermined.

Power lost by the heat source supply 210 may be measured every second, and the measured lost power may be transmitted to a processor (not shown), for example, a desktop computer.

The cutoff portion 220 may be disposed to be sealed in an upper portion of the internal chamber 200.

The cutoff portion 220 may include the covering material 222 and the thermal screen 224.

The covering material 222 may be detachably disposed in the internal chamber 200 or the spacer 202 of the internal chamber 200. The covering material 222 may include a polyethylene film. The covering material 222 may include a single layer or two layers of a polyethylene film, whereby the internal chamber 200 may be single-covered or double-covered.

The covering material 222 may prevent an outflow of heat emitted by the heat source supply 210 to an external portion of the internal chamber 200.

The thermal screen 224 may also be detachably disposed in the internal chamber 200 or the spacer 202 of the internal chamber 200. As illustrated in FIG. 1, the thermal screen 224 may be disposed below the covering material 222 to be separated from the covering material 222 in a vertical direction.

Similar to the covering material 222, the thermal screen 224 may also prevent an outflow of heat emitted by the heat source supply 210 to the external portion of the internal chamber 200.

The thermal screen 224 may include a multilayer thermal screen, white polyester, and white fabric polyester.

The multilayer thermal screen may include white polyester, polyethylene foam, and white fabric polyester. In detail, the multilayer thermal screen may be formed by layering 0.4-millimeter (mm)-thick white polyester, 1-mm-thick polyethylene foam, 0.25-mm-thick white fabric polyester, 1-mm-thick polyethylene foam, and 0.4-mm-thick white polyester. The multilayer thermal screen may be provided in a single layer or two layers in the apparatus 10.

The white polyester may also be provided in a single layer or two layers in the apparatus 10.

In addition, the white polyester and the white fabric polyester may be formed to be layered.

As described above, the covering material 222 or the thermal screen 224 of the cutoff portion 220 may be combined variously and thus, overall heat transfer coefficients with respect to combinations of the covering material 222 and the thermal screen 224 may be measured.

The sky radiation realization portion 230 may be disposed in an upper portion of the internal chamber 200. The sky radiation realization portion 230 may be disposed above the cutoff portion 220 provided in the internal chamber 200.

The sky radiation realization portion 230 may be disposed in the upper portion of the internal chamber 200 in a size that covers the entire internal chamber 200. The sky radiation realization portion 230 may be provided using stainless steel. In this example, the sky radiation realization portion 230 may be covered with aluminum foil for efficient radiant heat transfer of the covering material 222 or the thermal screen 224 of the cutoff portion 220.

The sky radiation realization portion 230 may be used to realize a configuration in which a sky radiation is considered or a configuration in which a sky radiation is disregarded. Further, the sky radiation realization portion 230 may realize a sky temperature.

A pipe 232 may be provided in the sky radiation realization portion 230. A working fluid may circulate through the pipe 232.

For example, when a refrigerant including R22 is injected as the working fluid, the refrigerant may decrease a surface temperature of the sky radiation realization portion 230 down to −30° C.

A difference between a sky temperature and an outside air temperature at night may average −20° C. When an internal temperature of the external chamber 100 is set to 0° C., a surface temperature of the cutoff portion 220 of the internal chamber 200 may need to be controlled and maintained to be −20° C.

In FIG. 1, only the pipe 232 is provided in the sky radiation realization portion 230. However, it may be obvious that in addition to the pipe 232, a refrigerant storage to store a refrigerant or a hose to be used to transfer a refrigerant may be further included in the sky radiation realization portion 230.

As described above, an environment similar to an outdoor environment may be realized indoors by the sky radiation realization portion 230. Thus, the apparatus 10 capable of performing indoor measurements may be provided.

To realize various covering conditions in the apparatus 10, the covering material 222 and the thermal screen 224 may be configured in various combinations. For example, the covering material 222 and the thermal screen 224 may be selected from a single layer of a covering material, two layers of a covering material, a multilayer thermal screen, white polyester, and white fabric polyester. In addition, the sky radiation realization portion 230 may be selectively applied or detached.

The following Table 1 lists examples of combinations of the covering material 222, the thermal screen 224, and the sky radiation realization portion 230.

TABLE 1

| Condition | Covering material | Thermal screen | Sky radiation realization portion |
|---|---|---|---|
| 1L | 1 layer | No | No |
| 1LS | 1 layer | No | Yes |
| 2L | 2 layers | No | No |
| 2LS | 2 layers | No | Yes |
| 3LM | 2 layers | 1 layer of multilayer thermal screen | No |
| 3LMS | 2 layers | 1 layer of multilayer thermal screen | Yes |
| 4LW | 2 layers | 2 layers of white polyester | No |
| 4LWS | 2 layers | 2 layers of white polyester | Yes |
| 4LFW | 2 layers | 1 layer of white fabric polyester + 1 layer of white polyester | No |
| 4LFWS | 2 layers | 1 layer of white fabric polyester + 1 layer of white polyester | Yes |
| 4LM | 2 layers | 2 layers of multilayer thermal screen | No |
| 4LMS | 2 layers | 2 layers of multilayer thermal screen | Yes |

In detail, the combinations of the cutoff portion 220 and the sky radiation realization portion 230 may be as follows. A first condition (1L) may correspond to a combination of a single layer of a covering material, no thermal screen, and no sky radiation realization portion. A second condition (1LS) may correspond to a combination of a single layer of a covering material, no thermal screen, and a sky radiation realization portion. A third condition (2L) may correspond to a combination of two layers of a covering material, no thermal screen, and no sky radiation realization portion. A fourth condition (2LS) may correspond to a combination of two layers of a covering material, no thermal screen, and a sky radiation realization portion. A fifth condition (3LM) may correspond to two layers of a covering material, a single layer of a multilayer thermal screen, and no sky radiation realization portion. A sixth condition (3LMS) may correspond to a combination of two layers of a covering material, a single layer of a multilayer thermal screen, and a sky radiation realization portion. A seventh condition (4LW) may correspond to a combination of two layers of a covering material, two layers of white polyester, and no sky radiation realization portion. An eighth condition (4LWS) may correspond to a combination of two layers of a covering material, two layers of polyester, and a sky radiation realization portion. A ninth condition (4LFW) may correspond to a combination of two layers of a covering material, a single layer of white fabric polyester, a single layer of white polyester, and no sky radiation realization portion. A tenth condition (4LFWS) may correspond to a combination of two layers of a covering material, a single layer of white fabric polyester, a single layer of white polyester, and a sky radiation realization portion. An eleventh condition (4LM) may correspond to two layers of a covering material, two layers of a multilayer thermal screen, and no sky radiation realization portion. A twelfth condition (4LMS) may correspond to a combination of two layers of a covering material, two layers of a multilayer thermal screen, and a sky radiation realization portion.

The temperature measurement portion 240 may be disposed internally and externally of the internal chamber 200 to measure an internal temperature and an external temperature of the internal chamber 200.

Temperature sensors may be disposed internally and externally of the side walls and the bottom surface of the internal chamber 200. The internal temperature and the external temperature of the internal chamber 200 may be determined based on an average of measured temperatures.

It is obvious that temperature measurements are to be performed after the temperature reaches equilibrium. By comparing the measured internal temperature to the measured external temperature of the internal chamber 200, a heat loss through the internal chamber 200 may be calculated. Thus, a method of performing a calculation based on an average of a plurality of measured temperatures may be efficient in reducing an error in calculation of an overall heat transfer coefficient.

The temperature adjustment portion 300 may be further included in the external chamber 100 to adjust an internal temperature of the external chamber 100.

The temperature adjustment portion 300 may adjust the internal temperature of the external chamber 100 to meet external conditions to be realized. For example, to realize the winter, the internal temperature of the external chamber 100 may be set to be relatively low. To realize the summer, the internal temperature of the external chamber 100 may be set to be relatively high.

Through the aforementioned configuration, the apparatus 10 may realize various combinations of the covering material 222 and the thermal screen 224 and measure an overall heat transfer coefficient, thereby suggesting a quantitative heat insulation performance of the covering material 222 or the thermal screen 224. In addition, the apparatus 10 may realize a sky radiation, thereby increasing an accuracy of the measured overall heat transfer coefficient. In particular, the apparatus 10 may be advantageous in that an indoor measurement of the overall heat transfer coefficient is possible.

Figure 2:
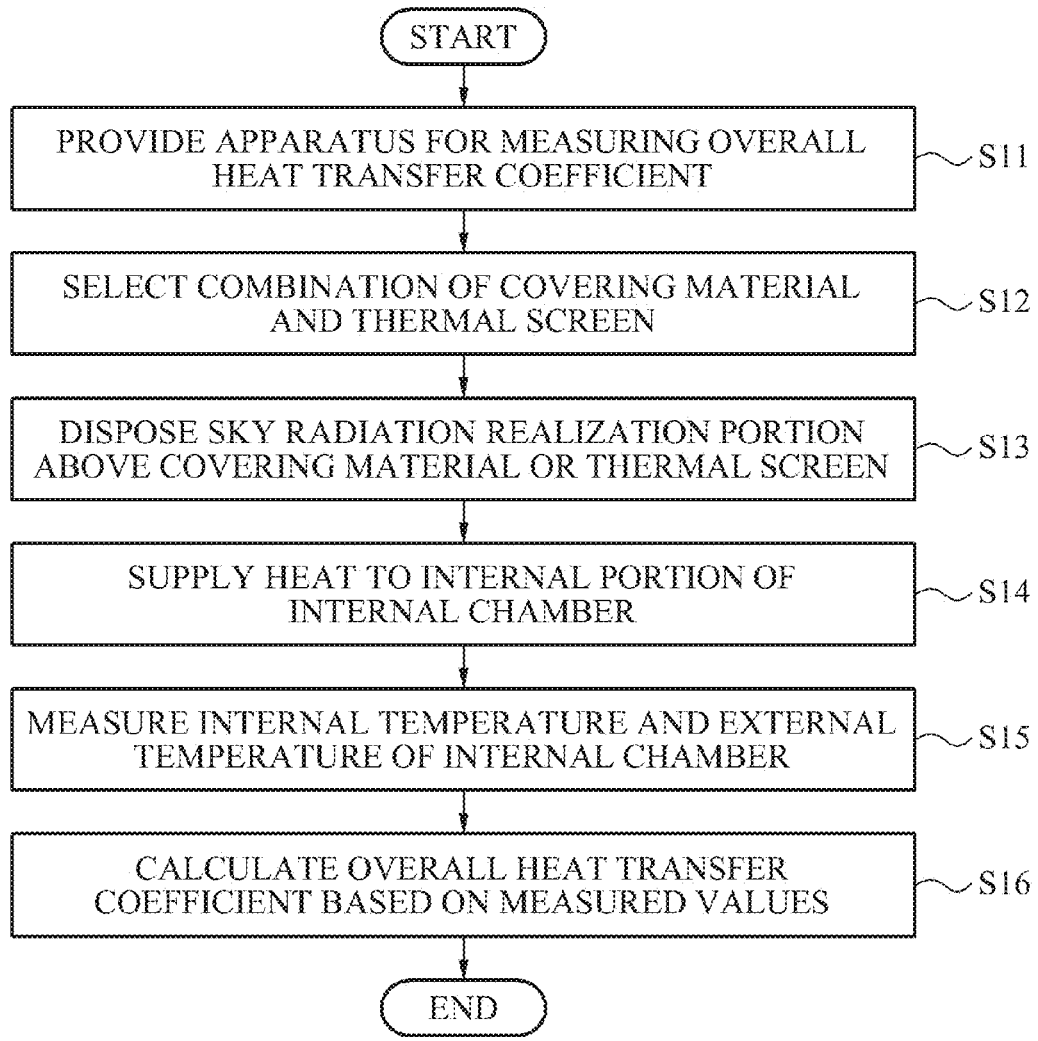
FIG. 2 is a flowchart illustrating a method of measuring an overall heat transfer coefficient according to an embodiment of the present invention.

FIG. 2 is a flowchart illustrating a method of measuring an overall heat transfer coefficient according to an embodiment of the present invention. Referring to FIG. 2, the method of measuring an overall heat transfer coefficient may be performed as follows.

In operation S11, an apparatus for measuring an overall heat transfer coefficient as described above may be provided indoors. In this example, an internal temperature of an external chamber may be controlled by a temperature adjustment portion. The external chamber may be manufactured using a heat insulation material and thus, the internal temperature of the external chamber may be maintained to be a set temperature.

In operation S12, a combination of a covering material and a thermal screen to be disposed in an upper portion of an internal chamber may be selected. The combination of the covering material and the thermal screen may be configured by referring to Table 1. The covering material and the thermal screen may be combined based on measurement conditions.

In operation S13, a sky radiation realization portion may be disposed above the covering material or the thermal screen to realize a sky temperature.

In this example, when a heat loss by a sky radiation is to be considered, a sky radiation realization portion may be provided. Conversely, when the heat loss by the sky radiation is to be disregarded, the sky radiation realization portion may not be provided. The provision of the sky radiation realization portion may be optional.

Hereinafter, a distribution of a sky temperature in response to an application of the sky radiation realization portion will be described. In this example, the sky temperature may refer to a temperature between a cutoff portion and the sky radiation realization portion.

Figure 3:
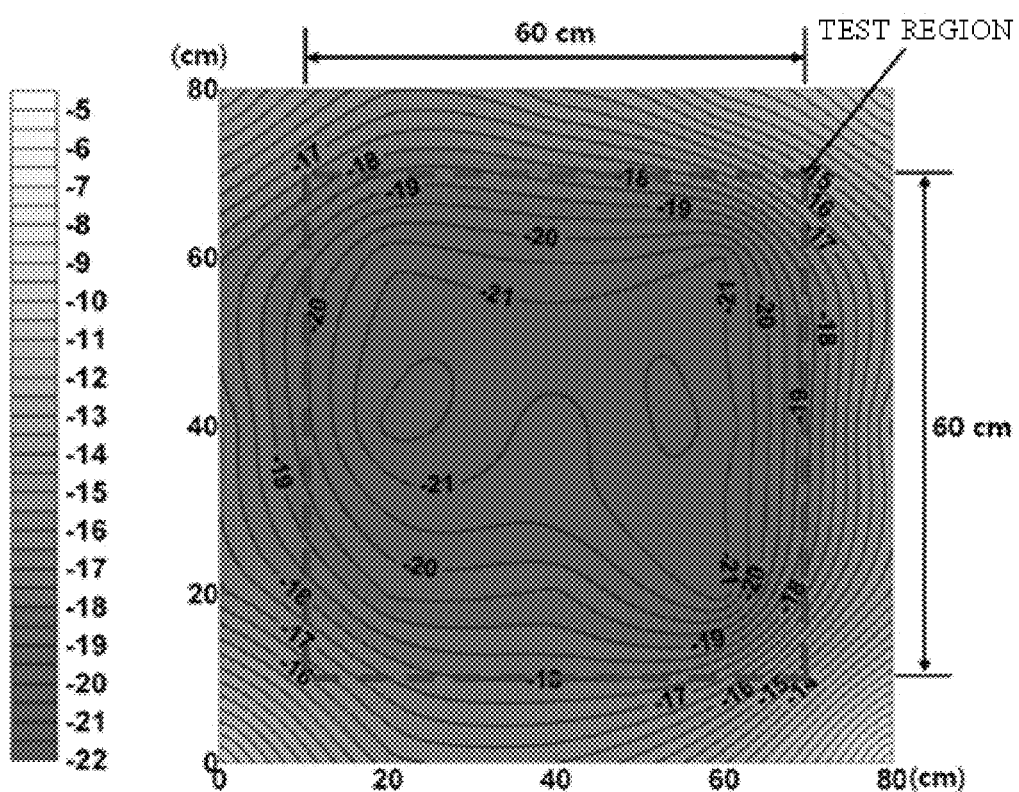
FIG. 3 illustrates a distribution of a sky temperature measured on a cutoff portion of an apparatus for measuring an overall heat transfer coefficient according to an embodiment of the present invention.

FIG. 3 illustrates a distribution of a sky temperature measured on a surface of a cutoff portion of an apparatus for measuring an overall heat transfer coefficient according to an embodiment of the present invention.

Referring to FIG. 3, a distribution of a sky temperature measured on a cutoff portion of an internal chamber when the sky temperature is controlled and maintained to be −20° C. is illustrated. In this example, the sky temperature may be controlled by injecting a refrigerant through a pipe provided in a sky radiation realization portion.

As a realization result of a sky radiation, a temperature of a 60 centimeters (cm)×60 cm test region on the cutoff portion may range from −18° C. to −22° C. (average −20° C.), which is similar to the controlled value.

As described above, the overall heat transfer coefficient may be measured by the apparatus for measuring an overall heat transfer coefficient by realizing sky temperature conditions.

When measurement preparations are completed, heat may be supplied to an internal portion of the internal chamber by a heat source supply disposed in the internal chamber, in operation S14.

When electricity is supplied from a power supply connected to the heat source supply, heat may be emitted from the heat source supply and an internal temperature of the internal chamber may increase, which makes a difference between the internal temperature and an external temperature of the internal chamber. The temperature may reach an equilibrium state in which the temperature barely changes, and heat may be continuously supplied to maintain such a state.

In operation S15, the internal temperature and the external temperature of the internal chamber may be measured in such a state. The temperatures may be measured by a plurality of sensors disposed internally and externally of the internal chamber.

Based on the temperatures measured by the respective sensors, an average of temperatures measured by sensors disposed internally of the internal chamber may be determined to be the internal temperature of the internal chamber, and an average of temperatures measured by sensors disposed externally of the internal chamber may be determined to be the external temperature of the internal chamber.

In operation S16, an overall heat transfer coefficient may be calculated based on the measured values.

In general, an overall heat transfer coefficient may be calculated as expressed by Equation 1.

$$U = \frac{Q}{A(T_i - T_o)} \quad \text{[Equation 1]}$$

In Equation 1, U denotes a heat transfer coefficient of a sample, for example, a covering material or a thermal screen. Q denotes energy supplied into a case in which the sample is provided. A denotes a cross-sectional area of the sample. $T_i$ denotes an internal temperature of the case. $T_o$ denotes an external temperature of the case.

Equation 1 may be applied to a case in which a heat loss is disregarded. Through Equation 1, it may be understood that the heat transfer coefficient may be calculated by dividing a quantity of heat by the cross-sectional area and a temperature difference.

However, in a case in which a heat loss is substantially considered, an overall heat transfer coefficient to be used to measure a heat insulation performance of a covering material or a thermal screen may be calculated as expressed by Equation 2.

$$U = \frac{Q_r - Q_w}{A(T_i - T_o)} \quad \text{[Equation 2]}$$

In Equation 2, $Q_r$ denotes a quantity of heat supplied by the heat source supply. $Q_w$ denotes a heat loss dissipated through walls of the internal chamber. A denotes a cross-sectional area of the covering material or the thermal screen. $T_i$ denotes an internal temperature of the internal chamber below the covering material or the thermal screen. $T_o$ denotes an external temperature of the internal chamber.

An overall heat transfer coefficient of the covering material or the thermal screen may be calculated by dividing a difference between the quantity of heat supplied by the heat source supply and a heat loss dissipated through the internal chamber by a difference between the internal temperature and the external temperature of the internal chamber and the cross-sectional area of the covering material or the thermal screen. In this example, the heat loss dissipated through the internal chamber may correspond to a heat loss dissipated through the covering material or the thermal screen.

In addition, the heat loss $Q_w$ dissipated through the walls of the internal chamber may be calculated as expressed by Equation 3.

$$Q_w = \frac{\lambda S_w(T_p - T_x)}{L_w} \quad \text{[Equation 3]}$$

In Equation 3, $\lambda$ denotes a thermal conductivity of a heat insulation material constituting the internal chamber. $S_w$ denotes a surface area of the walls of the internal chamber. $T_p$ denotes an internal surface temperature of the walls of the internal chamber. $T_x$ denotes an external surface temperature of the walls of the internal chamber. $L_w$ denotes a thickness of the internal chamber.

Through the simple equations provided above, the overall heat transfer coefficient may be obtained with relative ease. A relatively great overall heat transfer coefficient may indicate a relatively poor heat insulation performance of a combination of a covering material and a thermal screen, and a relatively small overall heat transfer coefficient may indicate a relatively excellent heat insulation performance of a combination of a covering material and a thermal screen.

Thus, a quantitative heat insulation performance of the covering material or the thermal screen provided in the internal chamber may be suggested.

In addition, according to the method of measuring an overall heat transfer coefficient, by realizing various covering conditions of a greenhouse, standards of a covering material or a thermal screen for a greenhouse may be established and a heating load of an actual greenhouse may be relatively accurately calculated.

The apparatus and method for measuring an overall heat transfer coefficient is described above. Hereinafter, experimental data obtained therethrough will be described.

Figure 4B:
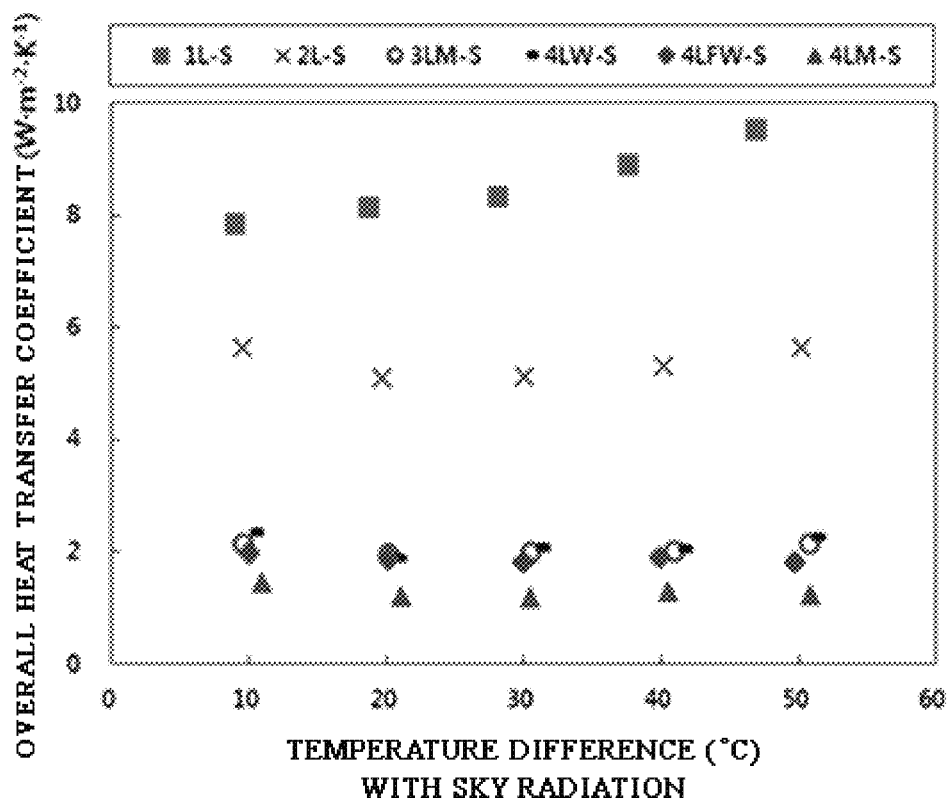

FIGS. 4A and 4B illustrate changes in an overall heat transfer coefficient with respect to a difference between an internal temperature and an external temperature of an internal chamber of an apparatus for measuring an overall heat transfer coefficient according to an embodiment of the present invention.

Referring to FIGS. 4A and 4B, it may be understood that the greater the difference between the internal temperature and the external temperature of the internal chamber, the higher the overall heat transfer coefficient. The increase in the overall heat transfer coefficient with respect to the temperature difference may result from an increased convective heat transfer coefficient.

The overall heat transfer coefficient may vary depending on the difference between the internal temperature and the external temperature of the internal chamber. Thus, to obtain an overall heat transfer coefficient of a covering material or a thermal screen, a determination of a specific temperature difference of the internal chamber may be required.

In a case of FIG. 4A in which a sky radiation is realized and in a case of FIG. 4B in which a sky radiation is not realized, a slope of an overall heat transfer coefficient of a single layer of a covering material (1L) and a slope of an overall heat transfer coefficient of two layers of a covering material (2L) with respect to temperature differences of 10° C., 20° C., 30° C., 40° C., and 50° C. are considerably greater than a slope of a combination (3LM) of two layers of a covering material and a single layer of a multilayer thermal screen, a slope of a combination (4LW) of two layers of a covering material and two layers of white polyester, a slope of a combination (4LFW) of two layers of a covering material, a single layer of white fabric polyester, and a single layer of white polyester, and a slope of a combination (4LM) of two layers of a covering material and two layers of a multilayer thermal screen.

However, in experiments in which a thermal screen is provided, the slopes of the overall heat transfer coefficients are almost parallel. 4LM has a smallest overall heat transfer coefficient, and is followed by 4LFW, 4LW, and 3LM sequentially. Accordingly, it may be understood that the combinations including a thermal screen are relatively excellent in terms of a greenhouse effect, when compared to the combinations not including a thermal screen.

Figure 5:
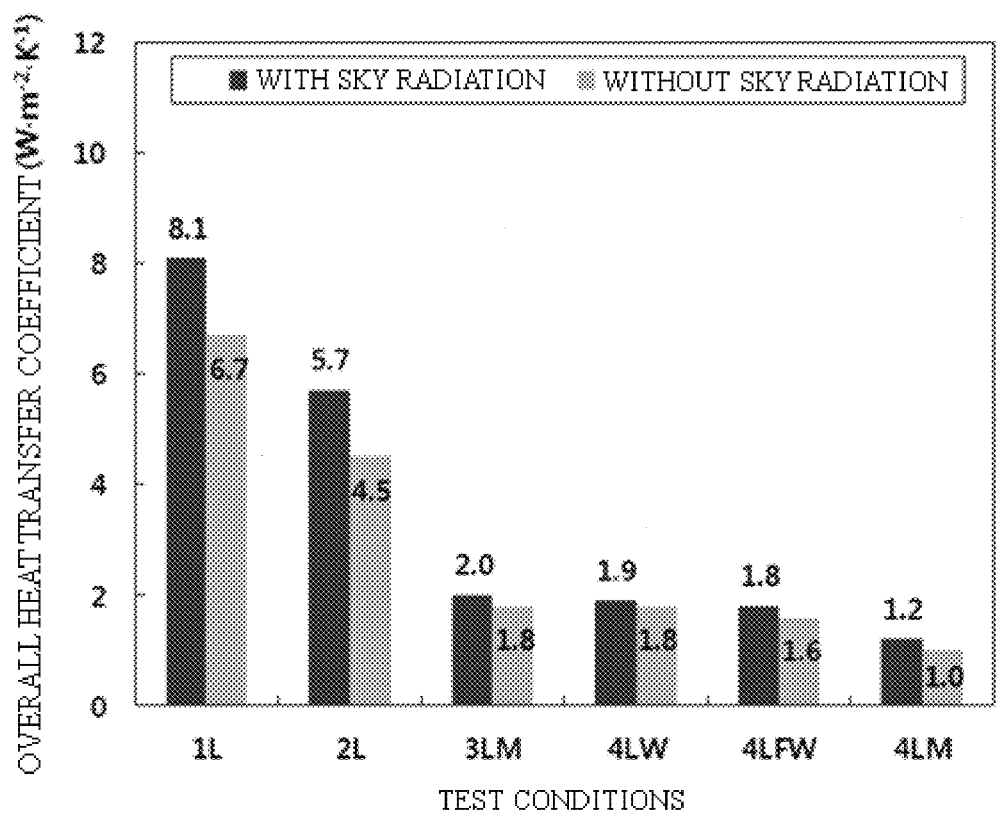
FIG. 5 is a bar graph illustrating overall heat transfer coefficients measured by an apparatus for measuring an overall heat transfer coefficient under test conditions according to an embodiment of the present invention.

FIG. 5 is a bar graph illustrating overall heat transfer coefficients measured by an apparatus for measuring an overall heat transfer coefficient under test conditions according to an embodiment of the present invention.

Referring to FIG. 5, it may be understood that an overall heat transfer coefficient measured when a sky radiation is realized is greater than that measured when a sky radiation is not realized by about 17% for 1L, 21% for 2L, 10% for 3LM, 5% for 4LW, 11% for 4LFW, and 17% for 4LM.

A heat loss of a covering material combined with a thermal screen by a sky radiation may change depending on a combination of the thermal screen and the covering material. A covering material combined with a thermal screen may have a much more modest heat loss than a covering material not combined with a thermal screen. From this, it may be understood that a heat loss through a covering material combined with a thermal screen is relatively modest and thus, a heat insulation performance thereof is relatively excellent.

Figure 6:
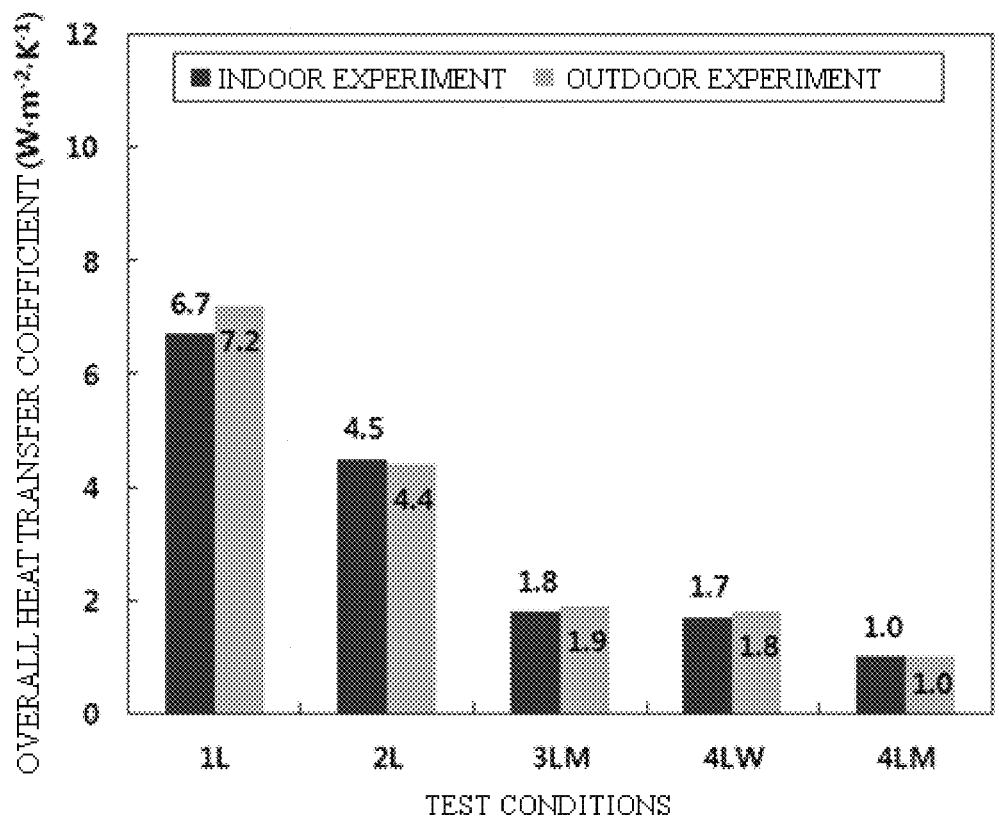
FIG. 6 is a bar graph illustrating overall heat transfer coefficients measured by an apparatus for measuring an overall heat transfer coefficient in a case in which a sky radiation is disregarded according to an embodiment of the present invention.

FIG. 6 is a bar graph illustrating overall heat transfer coefficients measured by an apparatus for measuring an overall heat transfer coefficient in a case in which a sky radiation is disregarded according to an embodiment of the present invention.

Referring to FIG. 6, overall heat transfer coefficients obtained through indoor experiments and outdoor experiments in a case in which a sky radiation is disregarded may be compared.

As a result of the comparison, the overall heat transfer coefficients in the indoor experiments are almost similar to the overall heat transfer coefficients in the outdoor experiments.

Thus, when an indoor experiment is performed using the apparatus for measuring an overall heat transfer coefficient while disregarding the sky radiation, reliable overall heat transfer coefficients of a covering material and a thermal screen may be obtained.

Figure 7:
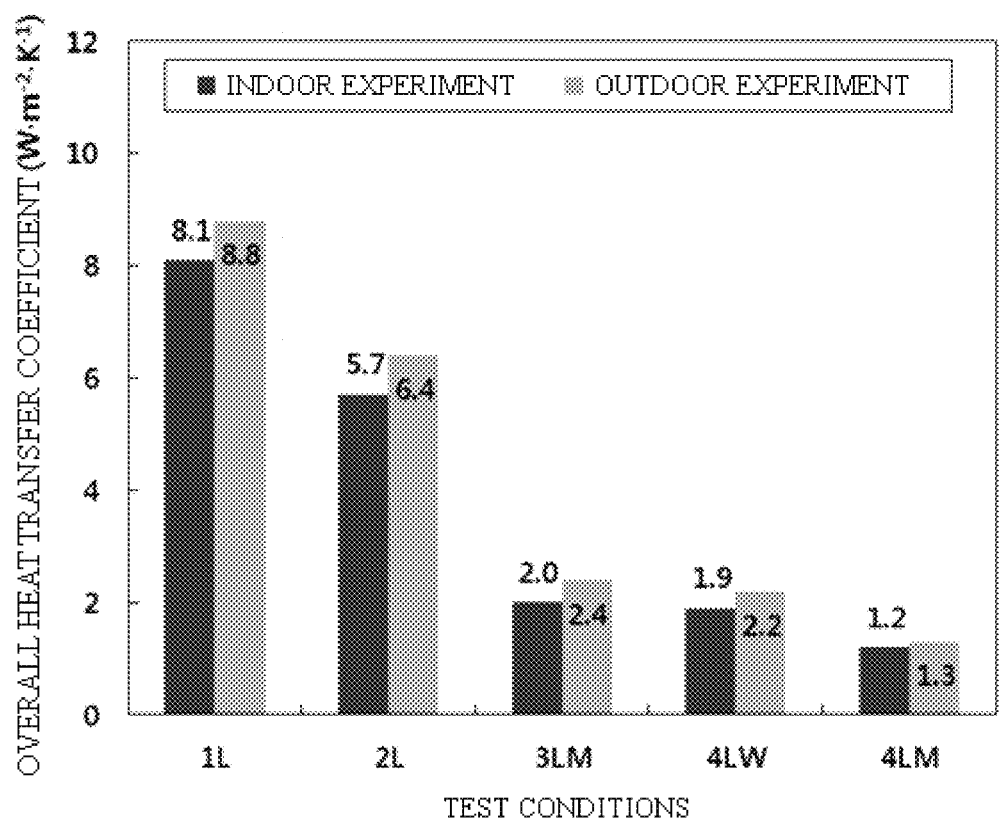
FIG. 7 is a bar graph illustrating overall heat transfer coefficients measured by an apparatus for measuring an overall heat transfer coefficient in a case in which a sky radiation is considered according to an embodiment of the present invention.

FIG. 7 is a bar graph illustrating overall heat transfer coefficients measured by an apparatus for measuring an overall heat transfer coefficient in a case in which a sky radiation is considered according to an embodiment of the present invention.

Referring to FIG. 7, overall heat transfer coefficients obtained through indoor experiments and outdoor experiments in a case in which the sky radiation is considered may be compared.

As a result of the comparison, the overall transfer coefficients in the indoor experiments are slightly different from the overall heat transfer coefficients in the outdoor experiments. However, since the difference is modest, the difference may be sufficiently reduced by controlling a sky radiation realization portion of the apparatus for measuring an overall heat transfer coefficient.

Such experiments may also be performed when comparing heat insulation performances of different types of covering materials or different types of thermal screens. Thus, heat transfer efficiencies of the covering materials or the thermal screens may be relatively simply compared. In addition, by controlling the sky radiation realization portion, outdoor conditions may be satisfied indoors, whereby experiments may be conveniently performed.

Accordingly, through the apparatus and method for measuring an overall heat transfer coefficient, an overall heat transfer characteristic of a covering material or a thermal screen may be quantitatively compared. Inversely, a suitable covering material or a suitable thermal screen may be selected to establish any greenhouse environment in an actual situation.

According to an embodiment of the present invention, an apparatus and method for measuring an overall heat transfer coefficient may suggest a quantitative heat insulation performance of a covering material or a thermal screen by measuring an overall heat transfer coefficient of the covering material or the thermal screen.

According to an embodiment of the present invention, an apparatus and method for measuring an overall heat transfer coefficient may establish standards of a covering material or a thermal screen for a greenhouse.

According to an embodiment of the present invention, an apparatus and method for measuring an overall heat transfer coefficient may accurately calculate a heating load of an actual greenhouse.

According to an embodiment of the present invention, an apparatus and method for measuring an overall heat transfer coefficient may simply realize various covering conditions of a greenhouse.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

The invention claimed is:

1. An apparatus for measuring an overall heat transfer coefficient, the apparatus comprising:
    an external chamber provided using a heat insulation material and comprising an internal space;
    an internal chamber disposed in the external chamber and having an opening upper portion;
    a heat source supply to supply heat to an internal portion of the internal chamber;
    a cutoff portion disposed in the upper portion of the internal chamber to seal the internal chamber and prevent an outflow of heat emitted from the heat source supply; and
    a temperature measurement portion disposed in an internal portion and an external portion of the internal chamber to measure an internal temperature and an external temperature of the internal chamber,
    wherein the cutoff portion realizes covering conditions indoors through a combination of a covering material and a thermal screen, and adjusts the external temperature of the internal chamber,
    wherein a sky radiation realization portion is provided above the cutoff portion to realize a sky radiation in order to provide an indoor environment similar to an outdoor environment,
    wherein a pipe is provided in the sky radiation realization portion to exchange heat, and
    wherein a sky temperature is realized through a working fluid circulating through the pipe.

2. The apparatus of claim 1, further comprising:
    a temperature adjustment portion disposed internally of the external chamber to adjust an internal temperature of the external chamber.

3. The apparatus of claim 1, wherein the covering material comprises a polyethylene film,
    the thermal screen comprises a multilayer thermal screen, white polyester, and white fabric polyester, and
    the sky radiation realization portion is provided using stainless steel.

4. The apparatus of claim 1, wherein a plurality of spacers is provided internally of the internal chamber to enable the covering material and the thermal screen to be detachably disposed and separated from each other in a vertical direction in the internal chamber.

5. The apparatus of claim 1, wherein the temperature measurement portion comprises a plurality of sensors and a means for calculating an average of temperatures measured by the plurality of sensors, and
    the plurality of sensors is disposed internally and externally of side walls and a bottom surface of the internal chamber to determine the internal temperature of the internal chamber by calculating an average of values measured inside the internal chamber, and determine the external temperature of the internal chamber by calculating an average of values measured outside the internal chamber.

6. A method of measuring an overall heat transfer coefficient, the method comprising:

providing an apparatus for measuring an overall heat transfer coefficient, the apparatus comprising an external chamber provided using a heat insulation material, and an internal chamber disposed in the external chamber;

selecting a combination of a covering material and a thermal screen to be disposed in an upper portion of the internal chamber;

disposing a sky radiation realization portion above the covering material or the thermal screen to realize a sky temperature in order to provide an indoor environment similar to an outdoor environment;

supplying heat to an internal portion of the internal chamber;

measuring an internal temperature and an external temperature of the internal chamber; and calculating the overall heat transfer coefficient based on the measured values, wherein a pipe is provided in the sky radiation realization portion to exchange heat, and wherein the sky temperature is realized through a working fluid circulating through the pipe.

7. The method of claim 6, wherein the calculating comprises calculating a heat loss dissipated through the internal chamber and calculating the overall heat transfer coefficient by dividing a difference between a quantity of heat supplied to the internal chamber and the heat loss dissipated through the internal chamber by a difference between the internal temperature and the external temperature of the internal chamber and an area of the covering material or the thermal screen.

* * * * *